(12) United States Patent
Alai

(10) Patent No.: US 9,731,053 B2
(45) Date of Patent: Aug. 15, 2017

(54) VACUBRASION: UNIVERSAL AIR FLOW REGULATOR AND ATTACHMENT FOR VACUUM ASSISTED MICRODERMABRASION

(71) Applicant: Nili Alai, Laguna Hills, CA (US)

(72) Inventor: Nili Alai, Laguna Hills, CA (US)

(*) Notice: Subject to any disclaimer, the term of this patent is extended or adjusted under 35 U.S.C. 154(b) by 294 days.

(21) Appl. No.: 13/862,300

(22) Filed: Apr. 12, 2013

(65) Prior Publication Data

US 2016/0129167 A1    May 12, 2016

Related U.S. Application Data

(60) Provisional application No. 61/624,236, filed on Apr. 13, 2012.

(51) Int. Cl.
| | | |
|---|---|---|
| *A61M 1/00* | (2006.01) | |
| *A61B 17/54* | (2006.01) | |
| *A61B 17/32* | (2006.01) | |

(52) U.S. Cl.
CPC ............ *A61M 1/0086* (2014.02); *A61B 17/54* (2013.01); *A61M 1/0047* (2013.01); *A61B 2017/320004* (2013.01); *A61B 2217/005* (2013.01); *A61B 2217/007* (2013.01)

(58) Field of Classification Search
CPC A61B 2017/00761; A61B 2017/00747; A61B 17/322; A61B 2017/3225; A61B 17/54; A47L 9/0072; A47L 9/02; A47L 9/068; A47L 9/0693; A47L 9/242; F16L 57/04; F16L 53/00; F16L 21/002; F01N 3/30; F01N 13/08; F01N 13/18; F01N 13/1844; A61M 1/0086; A61M 1/0047
See application file for complete search history.

(56) References Cited

U.S. PATENT DOCUMENTS

| | | | | |
|---|---|---|---|---|
| 7,234,733 | B2* | 6/2007 | Valentini | A47L 9/0072 15/321 |
| 7,527,305 | B2* | 5/2009 | Hyslop | F01N 3/30 137/217 |
| 8,113,543 | B1* | 2/2012 | Romani | A01K 13/001 15/419 |
| 2003/0187462 | A1* | 10/2003 | Chang | A61B 17/54 606/131 |
| 2004/0216264 | A1* | 11/2004 | Shaver et al. | 15/344 |
| 2008/0255586 | A1* | 10/2008 | Greenberg | A61B 17/54 606/131 |

* cited by examiner

*Primary Examiner* — Tuan V Nguyen
(74) *Attorney, Agent, or Firm* — Strategy IP, a professional Corporation

(57) ABSTRACT

The present invention provides a novel microdermabrasion system that provides safe and effective treatment for skin conditions such as acne, aging and sallow skin, fine wrinkles, surface skin scars, and other visually unappealing cosmetic skin disfigurements. This new invention provides a universal attachment and air flow/suction regulator which permits micro diamond chip based, crystal free microdermabrasion using a variety of standard vacuums and home based cleaning vacuums. Whereas currently available microdermabrasion devices have required a dedicated internal built in vacuum, this new invention allows the use of the universal attachment to most types of vacuums.

15 Claims, 4 Drawing Sheets

VACUBRASION: UNIVERSAL AIR FLOW REGULATOR AND ATTACHMENT FOR VACUUM ASSISTED MICRODERMABRASION

PRIORITY CLAIM

The application is an application for patent filed on Apr. 12, 2013 for a novel device. It follows PPA filed on Apr. 13, 2012 Application #61624236, EFS ID 12543516. Inventor claims domestic benefit of PPA as filed above.

FIELD OF THE INVENTIONS

The inventions described below relate the field of medical and cosmetic devices and methods, and more specifically to devices for performing dermabrasion, microdermabrasion, skin exfoliation, and skin and fat/cellulite massage procedures.

This invention provides for expanded home use of microdermabrasion and other suction stimulation of skin and subcutaneous tissues by consumers, professionals, and non-professionals using a vacuum source.

BACKGROUND OF THE INVENTIONS

The human skin consists of three layers. The epidermis or outermost layer is the thinnest layer and provides protection from the external environment. The dermis or middle layer primarily acts to provide structure and support. The third and innermost layer, which is the subcutaneous fat layer, provides insulation and acts as a shock absorber.

The epidermis is classically subdivided into 3 sub-layers, the outermost of which is the stratum corneum. The stratum corneum is made up of nonliving squamous cells and varies in thickness depending on the location on the body. It is typically thinnest on the eyelid skin and thickest on the palms and soles. In certain disease states like psoriasis the stratum corneum becomes thickened thereby causing a scalp, rash appearance to the skin. The epidermis becomes dulled and sallow as we age and accumulate sun damage. The epidermal pores can become plugged as in acne and keratosis pilaris. Keeping the epidermis healthy and properly exfoliated helps maintain overall skin appearance and a healthier skin glow. Unplugging epidermal pores through gentle exfoliation helps to open and unroof acne bumps and release the buildup of oils and skin debris. Gently exfoliating bumps of keratosis pilaris (the chicken or gooseflesh appearance on the upper arms and thighs) can help unroof the coiled, ingrown hairs and improve its overall appearance.

The stratum corneum may be thickened in areas of sun damage (heliodermatosis) and as result of skin aging. A dull and sallow appearance of the skin typically marks skin with prominent stratum corneum buildup. Fine skin wrinkles and creases exacerbate the age appearance of the skin. Minimally invasive techniques that help slough layers off the stratum corneum are called exfoliation. Exfoliative processes include physical methods like dermabrasion, microdermabrasion, laser resurfacing, dermaplaning, and chemical methods like superficial chemical peels. All of these processes have in common the ability to remove portions of the stratum corneum.

Mild physical exfoliation may be achieved using a variety of currently available methods including simply brushing the skin with a soft brush, wash cloth, or an abrasive material like BufPuf™ (3M Corporation, Minneapolis, Minn.) pads or pumice stones. More aggressive chemical exfoliation is generally performed using the topical application of a peeling agent like glycolic acid. Exfoliation (physical or chemical) often results in a cosmetically improved and rejuvenated appearance of the skin. Exfoliation is a relatively very safe technique that may most commonly be carried out at home; deeper or more aggressive exfoliation is carried out with a medical professional or with paraprofessionals like aestheticians. Deep exfoliation using surgical grade dermabrasion or deep chemical peels are only carried out by specially trained physicians and surgeons.

Dermaplaning is traditionally a technique wherein a sharp device called a dermatome is used to abrade away a controlled surface layer of skin. Dermatomes are hand-held blade devices that are designed to precisely shave off predetermined layers of the stratum corneum. Dermaplaning devices are fairly restricted sharps (large "butter knife" scalpel devices) and routinely designated to use by physicians, physician assistants, and other licensed professionals as deemed by each state.

True dermabrasion is typically a very invasive surgical procedure requiring administration of anesthetic prior to surgically scraping or manually sanding away much of the epidermis. Dermabrasion extends into the living part of the skin, typically beyond the full depth of the stratum corneum. This technique is used to improve the cosmetic appearance of deeper acne and facial scars as well as some tattoos. Dermabrasion is a very invasive surgical procedure performed only by physicians and cosmetic surgeons specifically trained in its use, and classically uses a motorized rotating disc with abrasive sand particles to sharply remove portions of the epidermis.

Microdermabrasion is a relatively safe and noninvasive technique for exfoliation and removal of the top layers of the stratum corneum. There are many types of microdermabrasion including 1) older crystal-based systems and 2) newer crystal-free systems. Microdermabrasion has been performed in the numbers of many millions of procedures all over the world and in the United States by aestheticians, medical assistants, and consumers for greater than 15 years.

In crystal microdermabrasion, aluminum oxide crystals flowing in an air stream are gently blown against the skin surface. In crystal microdermabrasion, there is essentially no bleeding, minimal complications, better compliance, and no need for local anesthesia or a skilled operator. In microdermabrasion, the speed, type, and density of crystals within the stream of air is related to the degree of micro-abrasion which can occur over a defined time period. Traditional crystal based microdermabrasion systems use a speed regulator to control the speed or velocity of the crystals. A bleed valve assists to introduce additional air into the stream of air and crystals. The net effect of the air bleed valve is a slowing of the suction and therefore a reduction in the strength of the abrasion. Crystal-based microdermabrasion units are very costly and relatively complex. U.S. Patent Application 20020090385 (Fox, et al.) discloses microdermabrasion applied with a crystalline emulsion. The carrier is a mixture of coated crystals. The coated crystals are formed by combining magnesium oxide, aluminum oxide or a combination of the two with methicone, adding a catalyst, such as ammonia, and mixing, then baking the resulting slurry mixture until the mixture is dry. The coated crystals thereby to stay in the emulsion in a carrier.

The "power peel" is another type of microdermabrasion. Available in the United States, it is also a method of "sandblasting" the skin. This procedure has been known to potentially help reduce the appearance of some types of acne scars and help reduce many other types of scars and skin imperfections. The power peel typically uses very fine and hard aluminum oxide crystals, which are air blasted at the skin with usually around 25 psi of air pressure. Safe operation of these devices requires the use of a limited number of passes or accurate control of pass speed to the target area. "Power peel" is intended to help remove only portions of the epidermis of the skin and therefore provides temporary improvement of the skin. It does not generally go deep or result in any alteration of scar formation. Systems include a vacuum apparatus to suction away unwanted crystal particles and exfoliated skin particles. Caution must be exercised to avoid inhalation of or ocular injury from the crystals by both the operator and the person undergoing treatment. U.S. Pat. No. 6,306,119 (Weber, et al.) further discusses this topic. Another variant of this methodology, i.e., the use of solid particles such as sand, alumina, or hard fibers, etc., is disclosed in U.S. Pat. No. 6,017,351 (Street) in which a cosmetic pad for use in removing surface detritus from the skin at pressures a lay person can apply in scrubbing the skin is comprised of a segment of lofty, fibrous, non-woven structure of mixed denier organic (e.g., nylon or polyester) crimped filaments bonded at contacting points with a binder such as thermosetting resin and containing finely divided, biocompatible, soft abrasive particles.

More recently introduced, crystal-free microdermabrasion techniques have evolved and involve no chemicals or crystals. This newer style of microdermabrasion utilizes a fixed particle abrasive on a tip which directly contacts the skin. A vacuum applies suction through the abrasive tip thereby gently exfoliating fine skin particles as the microdermabrasion wand is manually moved over the skin surface. These machines are still very expensive and moderately complex. Similar to crystal-based microdermabrasion, there is essentially no bleeding, minimal complications, better compliance, and no need for local anesthesia or a skilled operator in crystal-free microdermabrasion. In crystal-free microdermabrasion, the level of suction and the pressure of the wand and rate of manual wand movement over the skin primarily determine the degree of microabrasion which occurs over the treatment period.

The unparalleled safety and convenience of microdermabrasion has led to home use microdermabrasion machines, microdermabrasion cream kits, and hand-held microdermabrasion wands that are currently available including NuBrilliance™ (Wellquest International, Inc., New York, N.Y.). Many of the home-based machines are expensive and not affordable by the general consumer. Microdermabrasion creams are moderately expensive considering that they are 100% consumable and need frequent replenishment. In fact, the cream microdermabrasion systems often cost upwards of several hundred dollars per year and in time exceed the cost of a home-based microdermabrasion machine. The high-priced microdermabrasion units further make home microdermabrasion units inaccessible by many individuals and acne sufferers whose income does not permit this price range of expenditures. Many of the home units have been reported as having suboptimal mechanics with poor suction design that results in diminishing suction over time. The currently available home microdermabrasion devices require expenditures of several hundred dollars (average $230-$250 for NuBrilliance™) and acquisition of a small machine that may eventually fail and act as clutter.

In view of the foregoing, there exists a need in the current market for the design and development of a safe, simple, and relatively inexpensive microdermabrasion attachment device that a) can be used with minimal or no training by consumers and cosmetologists as well as more highly trained medical personnel and b) can be used with most commercially available home vacuums and c) is equipped with simple pressure controls that will minimize the likelihood of over abrading or irritating the skin.

SUMMARY

Various embodiments of the present invention provide a novel, simple, robust and relatively inexpensive microdermabrasion, dermabrasion, and skin care apparatus adapter for attachment to commercially available consumer grade vacuum sources.

Embodiments of the current invention would permit performing microdermabrasion essentially anywhere where there is access to a vacuum cleaner with a round outlet. Consumers using various embodiments of the new invention would not need to travel with large microdermabrasion equipment, they would have a universal attachment device that would fit into a small, book-sized box and would weigh less than ½ pound. The device would be sterilize-able and cleanable using alcohol and cold sterilizing solutions, thereby allowing the device to be used hygienically on multiple people. Current home microdermabrasion systems do not provide robust re-sterilize-able tips and therefore would require additional units for more than one individual's use. The new system would permit use on dry and moist or wet skin, and use with wet vacuums, whereas current microdermabrasion systems must be used only on dry skin. Additionally, this new application and design unit would permit use of this device for "wound vac" or suction to assist in wound healing.

Various embodiments of the invention will easily regulate and convert essentially any store bought vacuum cleaner (including wet/dry/or steamer vacuums) into a professional grade skin care apparatus that may be safely and effectively used for a variety of cosmetic and medical treatments with minimal to no training by untrained consumers and aestheticians, or in some cases by physicians and other trained professionals.

BRIEF DESCRIPTION OF THE DRAWINGS

In FIG. 1, a round outflow end 102 attaches to a standard 1¼ inch household vacuum hose (not shown, but readily understood).

In FIG. 2, a round intake 110 attaches to a rough metallic tip.

In FIG. 3, a universal ⅜ inch tip 106 comes in contact with the skin surface (not shown, but readily understood).

As shown in FIG. 4, a moveable airflow regulator 108 on a universal attachment opens and closes.

DETAILED DESCRIPTION OF THE INVENTIONS

Figure 1:
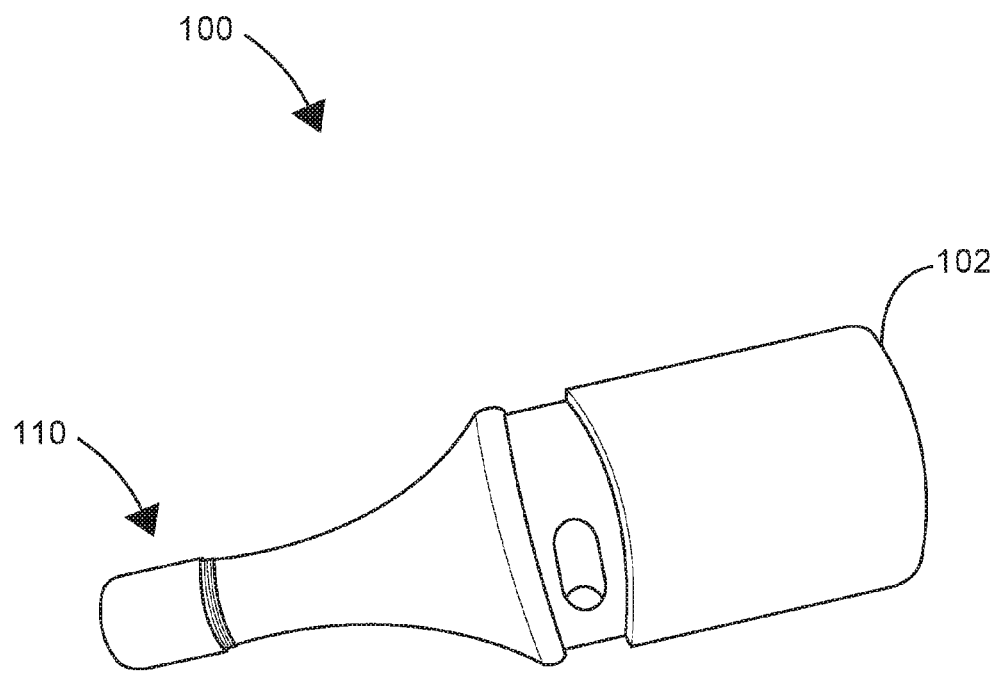
FIG. 1: Universal Adapter and air flow regulator showing outflow 102 (largest diameter end) which attaches to household vacuum.

The universal microdermabrasion attachment device of a first embodiment of the present invention generally comprises a small, non-motorized, cylindrical universal vacuum attachment 100 with an air flow/suction regulator 108. The cylindrical attachment wand is designed in a tapered fashion with a larger 1¼ inch diameter end 102 and a smaller ⅜ inch tip 110. The larger end 102 permits a one step attachment by a snap-in mechanism to the round tube outflow of a large number of household vacuum cleaners. The smaller end tip 110 permits a one step attachment by either a snap-on or screw-on mechanism 104 to a variety of standard sized microdermabrasion tips 106. The universal attachment cylinder and air flow regulator 108 allows for routine use of household vacuum cleaners and other house hold suction devices for microdermabrasion.

Universal cylinder attachment end 102 fits all 1¼ inch diameter vacuum cleaner wands or hoses including with Hoover, Eureka, Metrovac World Vacuums, etc.

Universal cylinder tapered attachment tip 110 of ⅜ inch size has threading 104 and attached to standard threaded microdermabrasion tips 106 and microdermabrasion wands and plastic tubes.

Universal cylinder attachment 100 has a built-in, slidable suction/air flow regulator 108 to adjust the pressure/vacuum from low to medium to high.

Universal cylinder tapered ⅜ inch tip 110 permits a versatile dual function for attaching directly to the snap-on or screw-on microdermabrasion tip 106, or indirectly through use of a standard microdermabrasion wand and tip through a ⅜ fitted long plastic tubing.

Air flow/suction regulator 108 is designed to allow maximum (High) microdermabrasion strength when the slider is in the almost fully closed position.

Air flow/suction regulator 108 is designed to permit minimal (Low) microdermabrasion strength when the slider is in the fully open position.

Universal attachment 100 may optionally have at its tip 110 (small) a replaceable filter disc to collect removed debris and help avoid possibility of two way transmission of debris collected from skin or inadvertent forward flow of vacuum collected debris.

FIG. 1 demonstrates the universal adapter 100 and air flow regulator 108 showing the outflow 102 (largest diameter end) which attaches onto a household vacuum. The cylindrical air regulator 108 reduces the outflow suction of consumer grade vacuums to a safe and effective level for cosmetic and medical grade skin treatments.

Figure 2:
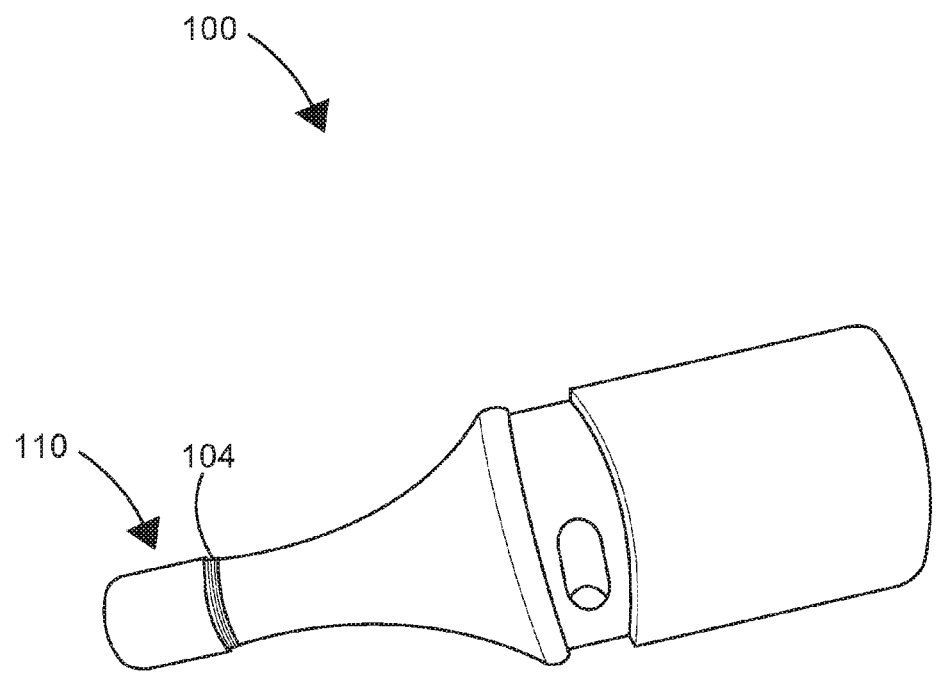
FIG. 2: Universal Adapter and air flow regulator showing intake 110 (smallest diameter end) which attaches to a rough surfaced, metal universal fit, screw-on or snap-on tip. Intake 110 comes in contact with skin.

FIG. 2 depicts the universal adapter 100 and air flow regulator 108 showing intake 110 (smallest diameter end) which attaches to a rough surfaced, metal universal fit, screw-on or snap-on tip 106. Intake 110 comes in contact with skin. Alternatively, this smaller intake end 110 may be attached to a ⅜ inch diameter tubing for an extended reach and flexibility.

Figure 3:
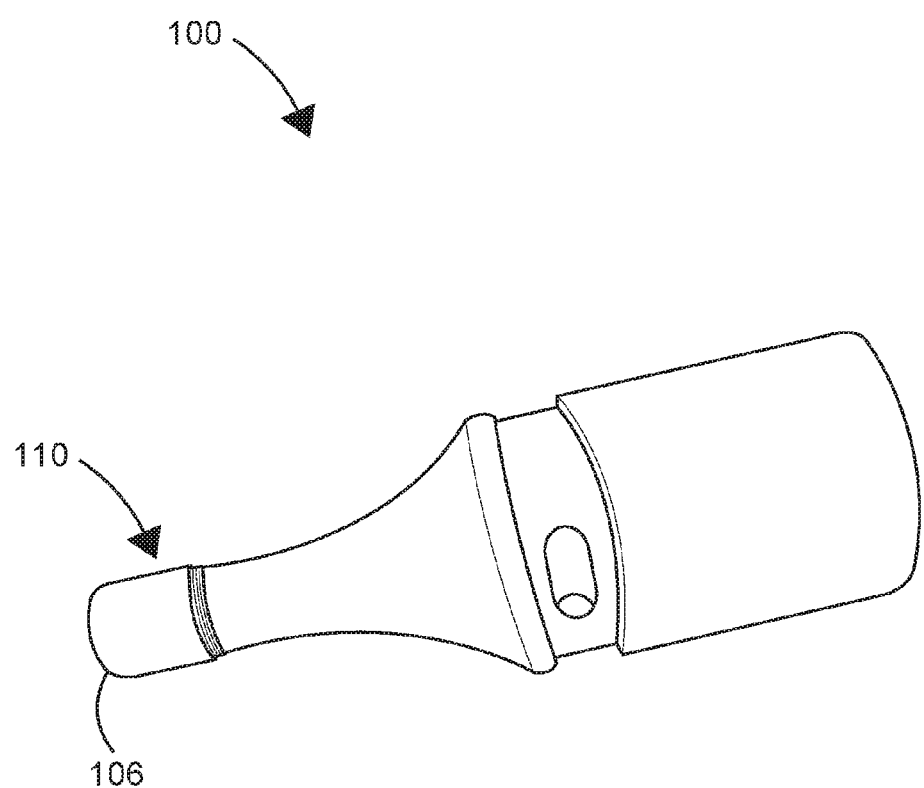
FIG. 3: Universal Adapter and air flow regulator showing intake 110 (smallest diameter end) which attaches to a rough surfaced, metal universal fit, screw-on tip.

FIG. 3 shows the universal adapter 100 and air flow regulator 108 showing the intake 110 (smallest diameter end), which attaches to a rough surfaced, metal or plastic universal fit, screw-on or snap-on tip 106. In alternative embodiments, this smaller intake end 110 may be attached to a ⅜ inch diameter tubing for an extended reach and flexibility.

Figure 4:
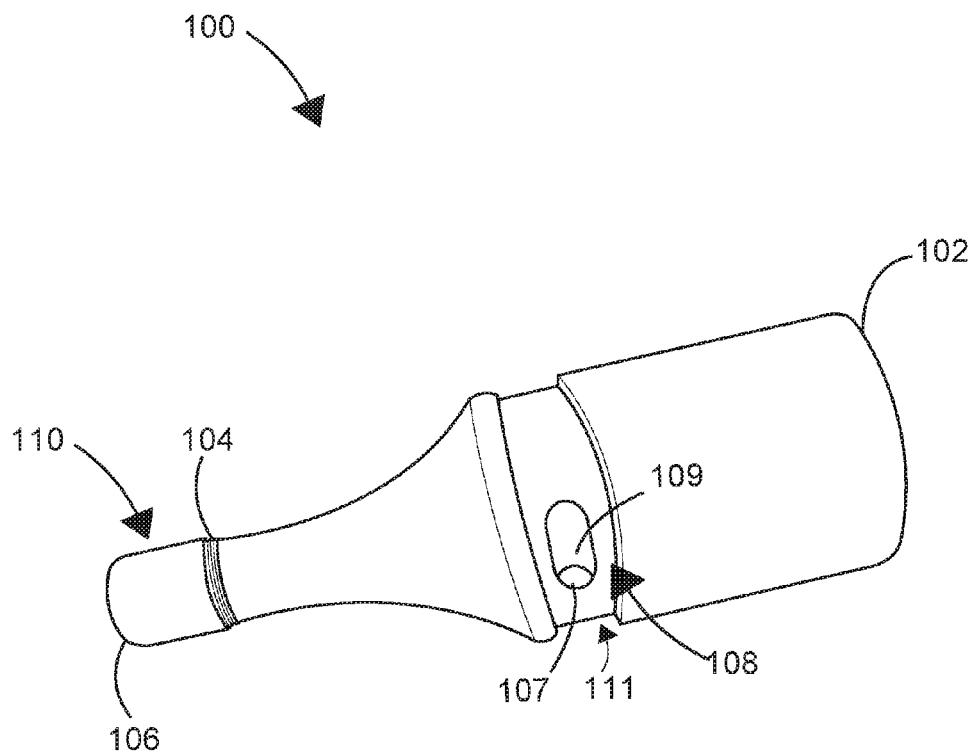
FIG. 4: Universal Adapter and air flow regulator showing movable airflow mechanism 108 which opens and closes thereby regulating vacuum strength.

FIG. 4 depicts the partially vented universal adapter 100 and air flow regulator 108 showing movable airflow mechanism 109 which opens and closes thereby regulating vacuum strength. The vents 107 in the fully open position will permit low suction; the vents 107 in the fully or nearly closed position will enable strong suction. The universal adapter 100 will have one small vent 111 open at all times to permit adequate air flow to the vacuum and avoid machine overheating. In the embodiment shown in FIG. 4, one small vent 111 is located on the back side of the adapter 100, which can be seen through the vent 107 on the front side of the adapter 100.

The basic apparatus comprises a small, non-motorized universal attachment 100 and air flow/suction regulator 108 which attaches to the round outflow opening of most standard vacuum cleaners. This universal attachment 100 and air/flow regulator 108 is a tapered cylinder which attaches at its largest diameter 102 (1.25 inches) directly to the vacuum source and attaches at its smallest diameter 110 (⅜ inch) to universal skin exfoliating attachments 106 which have a treatment effective covering such as abrasive materials, cloth, brush bristles, massaging projections, etc.

The cylinder is non-threaded at its largest diameter 110 (1.25 inches) and fits directly to the vacuum source as a snap-in method. The cylinder at its tapered end 110 is ⅜ inch and partially threaded 104 thereby allowing easy attachment at this tapered end 110 either directly to a multitude of universal microdermabrasion wands 106 or indirectly to other microdermabrasion wands through ⅜ inch fitted plastic tubing.

The tapered cylindrical apparatus 100 is made of 2 types of available materials including stainless steel or plastic has at its midsection a movable regulator 108 which modulates the airflow and suction through the body of the cylinder. The adjustable suction regulator has multiple notches that allow for variable levels of suction from low, medium, to high. The cylinder in its highest setting does not close fully and has a small opening 111 which permits release of partial suction from the cylinder. These air and suction regulators permit an adjustable air flow and modulation of the strength of suction at the skin surface.

In basic use, the tapered (⅜ inch) end 110 of the universal attachment cylinder 100 can directly attach to a screw-top or snap-on standard fit microdermabrasion tip 106. In extended use, the tapered cylindrical apparatus permits attachment of standard commercially available crystal-free microdermabrasion wands through clear plastic tubing. Various lengths of plastic tubing fitting an outflow of ⅜ inch may be fitted on to the tapered opening 110 of the cylinder and used to attach a large selection of types of standard commercially used microdermabrasion wands.

In standard operation, crystal-free microdermabrasion requires a rough metallic tip with fine abrasive material, often fine diamond chips and much less commonly adherent abrasive salts. Crystal-free microdermabrasion does not use any chemicals and uses the force of suction and fine abrasive materials to naturally abrade away superficial layers of the top layers of the skin (stratum corneum).

The universal attachment 100 described in this invention does not itself come in contact with the skin, and it does not have any abrasive properties itself. The universal attachment 100 and air flow/suction regulator 108 allow for the connection of a large variety of household vacuums with a round 1.25 inch outlet with a host of standard microdermabrasion tips and wands 106.

ALTERNATIVE EMBODIMENTS OF THE PRESENT INVENTION

With respect to the above descriptions, it is to be realized that the optimum dimensional relationships for the parts of the invention, to include variations in size, materials, shape, form, function, manner, color, and use are deemed readily apparent and obvious to one skilled in the art, and all equivalent relationships to those illustrated in the drawings and described in the specification are intended to be encompassed by the present invention.

In addition, accessory features may be incorporated within the apparatus such as specialized adapters intended for other vacuum types like Dyson, other specialized larger adapters intended for massage and exfoliation of larger body areas, and of other adjustable valves for regulating the airflow. Furthermore, a universal and multi-sized adapter may be provided on the apparatus so that the apparatus is tightly attached to a variety of suction sources including breast pumps. All of these modifications may be provided on the present description as described in this specification and still remain within the spirit and scope of the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, while still falling within the spirit and scope of the invention.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

I claim:

1. An apparatus for converting a commercially available vacuum source to microdermabrasion machines for suction and skin exfoliation comprising:
   a hollow, substantially cylindrical member having a large open end, a small open end, and at least one vent, the large end and the small end connected by an annular space through the hollow member; and
   a slidable regulator slidably attached to the cylindrical member;
   wherein the slidable regulator slides over the vent to variably obstruct the at least one vent when in a closed position and to open the at least one vent when in an opened position, and wherein the cylindrical member further includes an open vent that remains open when the slidable regulator is in a closed position.

2. The apparatus of claim 1, wherein the cylindrical member includes at least one hollow tube.

3. The apparatus of claim 1, wherein the slidable regulator is configured to partially close the at least one vent when in a partially closed position.

4. The apparatus of claim 1, wherein when the apparatus is attached to an operating vacuum source, the opened position of the slidable regulator enables a light suction level and the closed position of the slidable regulator enables a strong suction level.

5. The apparatus of claim 1, wherein the large end is adapted to attach to a standard vacuum cleaner hose.

6. The apparatus of claim 1, wherein the small end is adapted to attach to a microdermabrasion device.

7. The apparatus of claim 1, wherein the small end is threaded.

8. The apparatus of claim 1, wherein the commercially available vacuum source is selected from the group consisting of commercially available vacuum cleaners, wet/dry vacuum cleaners, steam vacuum cleaners, and vacuum pumps.

9. An apparatus for attachment to a vacuum source comprising:
   a tapered hollow cylinder including a first open end, a second open end, an open vent port, and at least one closable vent port, the first open end and the second open end connected by an annular space through the hollow member;
   a microdermabrasion device releasably coupled to the second open end; and
   a moveable air flow regulator coupled to the hollow cylinder;
   wherein:
      the first open end is adapted to attach to the vacuum source and
      the moveable air flow regulator is adjustable to regulate air flow through the apparatus by at least partially covering and uncovering the at least one closable vent port on the hollow cylinder.

10. The apparatus of claim 9, wherein the second open end is threaded.

11. The apparatus of claim 9, wherein the hollow cylinder includes at least one hollow tube.

12. The apparatus of claim 9, wherein the first open end is adapted to directly attach to a standard vacuum hose of the vacuum source.

13. A universal adapter to adjust air flow and regulate suction from a store bought, commercially available wet/dry, steam vacuum, or standard dry vacuum source to medical and cosmetic skin treatment devices comprising:
   a hollow, substantially cylindrical member having a large end and a small end, the large end and the small end connected by an annular space through the hollow member;
   at least one vent in the hollow cylindrical member capable of being closed or opened to adjust the level of suction;
   an open vent not closable by the movable air flow mechanism; and
   a movable air flow mechanism movably coupled to the cylindrical member and configured to variably close and open the at least one vent;
   wherein:
      the large end is adapted to attach to a standard vacuum hose,
      the small end is adapted to attach to a device selected from the group consisting of exfoliating medium, abrasive tip, skin rolling device, and wound suction cups.

14. The universal adapter of claim 13, wherein the cylindrical member includes at least one hollow tube.

15. The apparatus of claim 13, wherein the small end is threaded.

* * * * *